United States Patent [19]

Sorenson et al.

[11] 4,099,528
[45] Jul. 11, 1978

[54] DOUBLE LUMEN CANNULA

[75] Inventors: James L. Sorenson; Karl A. Pannier, Jr., both of Salt Lake City; Gordon S. Reynolds, Bountiful, all of Utah

[73] Assignee: Sorenson Research Co., Inc., Salt Lake City, Utah

[21] Appl. No.: 769,591

[22] Filed: Feb. 17, 1977

[51] Int. Cl.² .................. A61M 5/00; A61M 25/00
[52] U.S. Cl. .................. 128/214.4; 128/348; 128/DIG. 16
[58] Field of Search .......... 128/214 R, 214.4, 221, 128/DIG. 16, 347, 348

[56] References Cited

U.S. PATENT DOCUMENTS

| | | | |
|---|---|---|---|
| 3,220,411 | 11/1965 | Czorny | 128/214.4 |
| 3,610,226 | 10/1971 | Albisser | 128/214 R |
| 4,000,739 | 1/1977 | Stevens | 128/214.4 |
| 4,014,333 | 3/1977 | McIntyre | 128/214.4 X |
| 4,022,219 | 5/1977 | Basta | 128/351 |
| 4,054,136 | 10/1977 | Zeppelin | 128/214.4 |

OTHER PUBLICATIONS

Kruger, IBM Tech. Disclosure Bulletin, vol. 19, No. 4, Sep. 1976, pp. 1174–1175.

*Primary Examiner*—Dalton L. Truluck
*Attorney, Agent, or Firm*—H. Ross Workman; J. Winslow Young

[57] ABSTRACT

A double lumen cannula mounted upon a hub and constructed to penetrate the human vascular system, the cannula assembly having an interior cannula and an exterior cannula spaced from the interior cannula. A bushing is normally situated in the space between the interior and exterior cannula which bushing facilitates venipuncture without damaging the tissue. After venipuncture, the bushing is removable from the space between the interior and exterior cannulae by withdrawing the bushing from the cannulae through the hub.

8 Claims, 4 Drawing Figures

DOUBLE LUMEN CANNULA

BACKGROUND

1. Field of the Invention

The present invention relates to a cannula for medical use and more particularly to a double lumen cannula for independently conducting fluids into and out of a venipuncture site through two separate passageways.

2. The Prior Art

Double lumen cannulae are well known in the art. The best known advantage offered by double lumen cannulae is the ability to separately inject fluids into a blood vessel and withdraw fluids from a blood vessel through a single venipuncture.

The most common double lumen cannulae consist of a single tube with a horizontal division of the tube which places the lumens of the cannulae in immediate juxtaposition. Unfortunately, however, the construction of such double lumen cannulae is expensive, time consuming and unreliable.

The least expensive and most reliable construction of the double lumen cannulae is in the form of concentric lumens disposed telescopically one within the other. Especially in using the cannulae for single needle dialysis, it is preferred to have one of the cannula lumen project substantially beyond the other. The problems with such telescopic construction are apparent, however, when it is observed that both cannula must be used to penetrate the skin during venipuncture. Unless there is a smooth contour between the interior and exterior cannula, the venipuncture is both difficult and painful. On the other hand, if the telescoping cannulae present an exteriorly smooth surface for venipuncture, there is insufficient passageway for fluid to flow easily between the lumen. Accordingly, until this present invention, the construction of a safe, effective and comparatively painless double lumen cannula having telescoping lumen has not been known.

BRIEF SUMMARY AND OBJECTS OF THE INVENTION

The present invention comprises a series of telescoping members presenting an efficient venipuncture device. After venipuncture, by simple removal of a stylet needle and a bushing, an effective double lumen cannula is found in proper location within a patient's vein.

It is, therefore, a primary object of the present invention to provide an improved double lumen cannula.

It is another object of the present invention to provide a novel double lumen cannula assembly which has one lumen projecting beyond the other and which is safely and easily inserted into the cardiovascular system during venipuncture.

Another primary object of the present invention is to provide a double lumen cannula assembly having a contoured gasket which is used to facilitate introduction of the cannula assembly into the cardiovascular system during venipuncture and which can be removed to open a passageway between cannula lumen.

These and other objects and features of the present invention will become more fully apparent from the following description and appended claims taken in conjunction with the accompanying drawing.

DETAILED DESCRIPTION OF THE PREFERRED EMBODIMENTS

Figure 1:
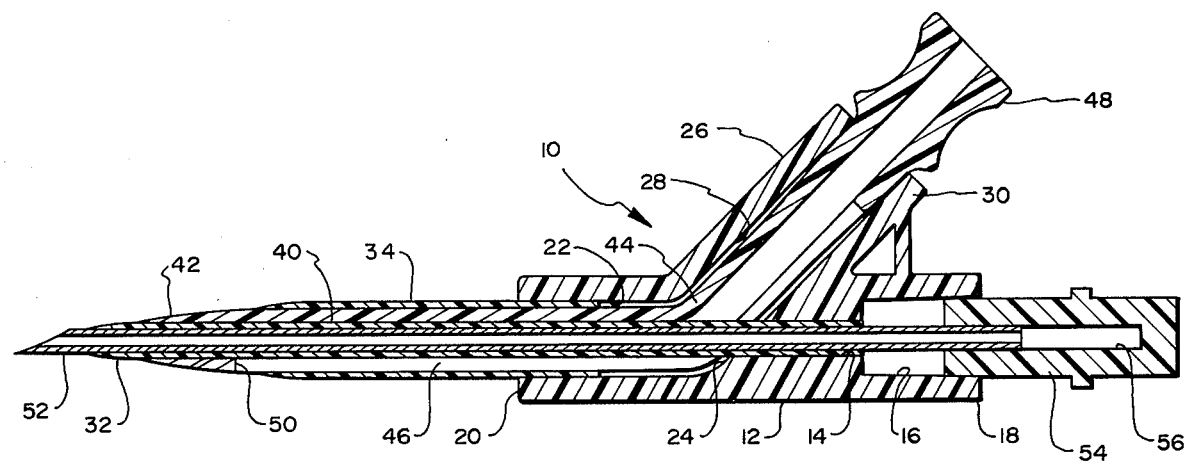
FIG. 1 is a longitudinal cross section of one presently preferred double lumen cannula assembly with stylet needle and gasket in initial position.
Figure 2:
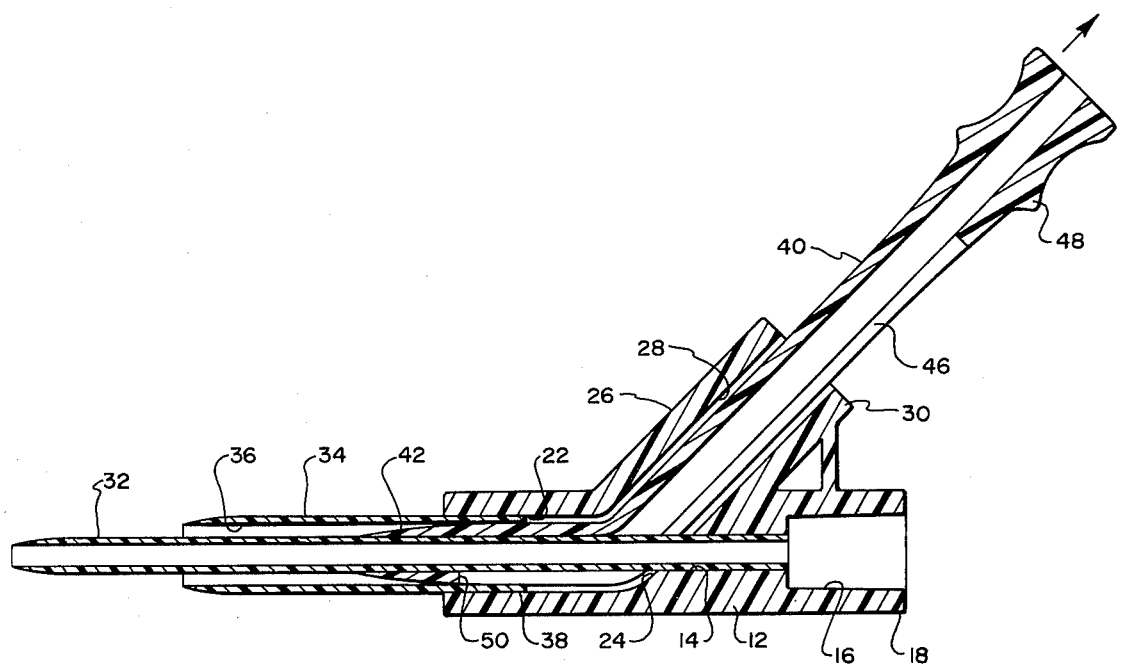
FIG. 2 is a longitudinal cross section of the cannula embodiment of FIG. 1 with the stylet needle removed and the bushing in a partially removed position.
Figure 3:
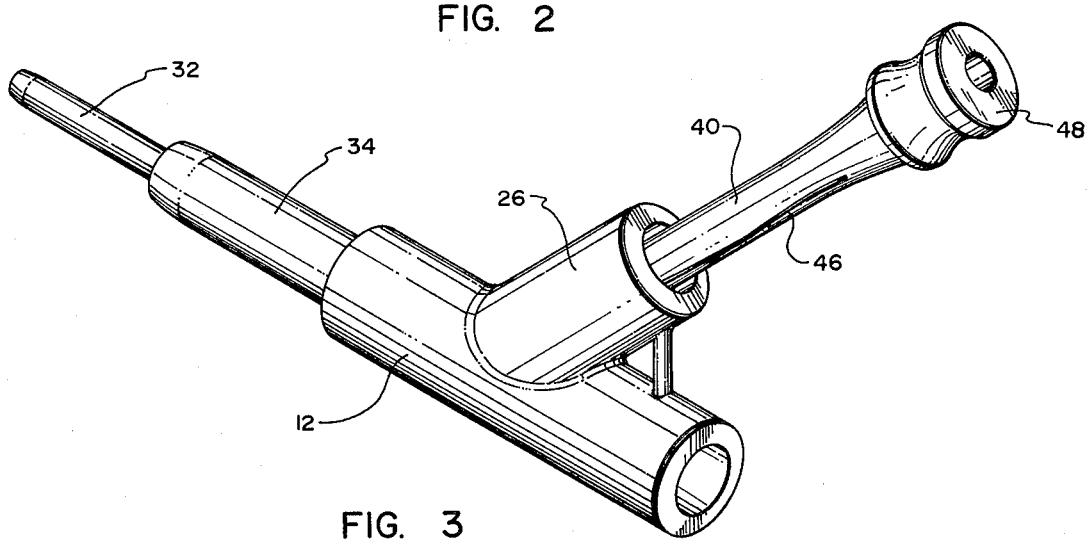
FIG. 3 is a perspective illustration of the cannula embodiment of FIG. 2 illustrating the bushing in its partially removed position.

Reference is now made to the drawing wherein like parts are designated with like numerals throughout. Referring more particularly to FIGS. 1–3, a cannula assembly generally designated 10 comprises a hub 12 having an axial bore 14 therethrough. The bore 14 is diametrally enlarged at 16 and opens at the trailing end 18 of the hub 12. The diametrally enlarged portion 16 forms a female coupling for conventional intravenous sets and the like. The leading end 20 of the hub 12 also has a diametrally enlarged bore 22 which defines an upwardly directed ramp surface 24.

The hub 12 presents an angularly directed branch 26 defining a hollow 28. The hollow 28 opens at the trailing end 30 of the branch 26 and also opens directly into the enlarged bore 22 near the leading end 20 of the hub 12. The hollow 28 of the branch 26 is sized and configurated so as to intersect the bore 22 at the ramp surface 24. Thus, a bifurcated passageway consisting of the bore 22, hollow 28 and bore 14 is defined by the hub 12 and angularly directed branch 26.

It should be observed that while the branch 26, in the illustrated embodiment, is oriented at approximately 45° with respect to the horizontal axis of the hub 12, any suitable angular orientation could be used.

As best shown in FIG. 2, the assembly 10 includes an interior cannula 32 which is mounted within the hub 12 at the location of the bore 14. The cannula 32 opens into the diametrally enlarged bore 16 so that open fluid communication can exist between the hollow of the interior cannula 32 and any infusion set (not shown) coupled at the trailing end 18 of the hub 12.

An exterior cannula 34 is mounted upon the hub 12 at the bore 22 so as to be forward of the branch 26. The exterior cannula 34 is coaxial with the interior cannula 32 and has an inside dimension which is diametrally enlarged over the outside dimension of the interior cannula 32. Thus, a passageway 36 normally exists between the exterior cannula 34 and the interior cannula 32. The passageway 36 opens at the trailing end 38 of the cannula 34 directly into the hollow 28 of the branch 26. It can thus be observed that the hollow 28 and the bore 22 communicate directly with the passageway 36. When an infusion set is coupled to the trailing end 30 of the branch 26, a direct fluid path exists along the hollow 28, bore 22 and passageway 36. Observe that this fluid path is completely separate and distinct from the fluid path through the hollow of cannula 32.

The length of the interior cannula 32 is selected to project noticeably beyond the leading end of the exterior cannula 34. Accordingly, when the cannula assembly 10 is used for procedures such as hemodialysis, blood can be withdrawn through one of the cannula 32 or 34 and returned through the other cannula 32 or 34 with minimal admixing. This construction has been found to be surprisingly effective in circulating blood into and out of the patient. Nevertheless, the configuration as illustrated in FIGS. 2 and 3 is not easily susceptible to venipuncture because of the noticeable size differential between the cannulae 32 and 34. Accordingly, a bushing 40 is temporarily interposed in the passageway 36 to facilitate venipuncture. The bushing 40 is constructed of a flexible plastic material and has a tapered leading end 42. In its fully assembled configuration illustrated in FIG. 1, the bushing 40 has a length which is greater than the exterior cannula 34 but less than the exterior cannula 32. Moreover, the cannulae 32 and 34 and bushing 40 are all correspondingly tapered. Accordingly, the cannula 32 when surmounted by both the bushing 40 and the exterior cannula 34 present an efficient surface for venipuncture.

The trailing end of the bushing 40 rests within the hollow 28 of the branch 26 and is bent at 44 into coaxial alignment with the cannulae 32 and 34. At the bend 44, the bushing 40 rests against the ramp surface 24. Significantly, the ramp surface 24 provides sufficient friction that the bushing 40 will resist displacement rearwardly relative to the cannulae 32 and 34 during venipuncture.

The bushing 40 has an axial slit 46 on the underside thereof which slit permits the interior cannula 32 to pass through the bushing 40 when the bushing is displaced in the direction of the arrow as shown in FIG. 2. Also, the bushing 40 has a diametrally enlarged finger accessible member 48 which is initially attached to the branch 26 in press-fit relation.

After venipuncture, the bushing 40 may be withdrawn from the passageway 36 by grasping the member 48 and withdrawing the bushing 40 from the passageway 36. During withdrawal, the interior cannula 32 separates the bushing 40 at the slit 46 as the bushing moves against the ramp surface 24 during withdrawal.

If desired, the slit 46 may terminate at 50 adjacent the tapered leading end 42. Thus the tapered leading end can present a smoother surface during venipuncture and, upon withdrawal, the tapered leading end will be ruptured by the force exerted through the bushing 40 where the tapered leading end meets the interior cannula 32 at the ramp surface 24.

In the illustrated embodiment, both the interior and exterior cannula are made of a comparatively soft medical grade plastic. Accordingly, in order to lend strength to the cannulae during venipuncture, a stylet needle 52 may be used to lend strength and rigidity to the cannulae 32 and 36 during venipuncture. The stylet needle 52, formed of conventional needle stock is coaxially disposed within the interior of the cannula 32. The stylet needle 52 is mounted at its trailing end into a plastic hub 54 in conventional fashion. If desired, the hub 54 may provide a hollow 56 utilized to observe blood flashback after successful venipuncture. Clearly, if cannula 32 is sharpened and sufficiently rigid, the stylet needle 52 may be omitted.

Upon successful completion of the venipuncture, the bushing may be removed as illustrated in FIG. 2 to open the passageway 36 to the coupling site at the trailing end 30 of the branch 26. It is presently preferred that the bushing 40 be removed while needle 52 remains in place to give support to the cannula 32 as the bushing 40 is separated therefrom in the vicinity of ramp surface 24.

Thereafter, hub 12 is grasped between the fingers and the hub 54 axially withdrawn toward the right as shown in FIG. 1. The hub 54 and attached needle 52 will then be withdrawn to open the interior cannula 32 directly into the coupling site at the trailing end 18.

Figure 4:
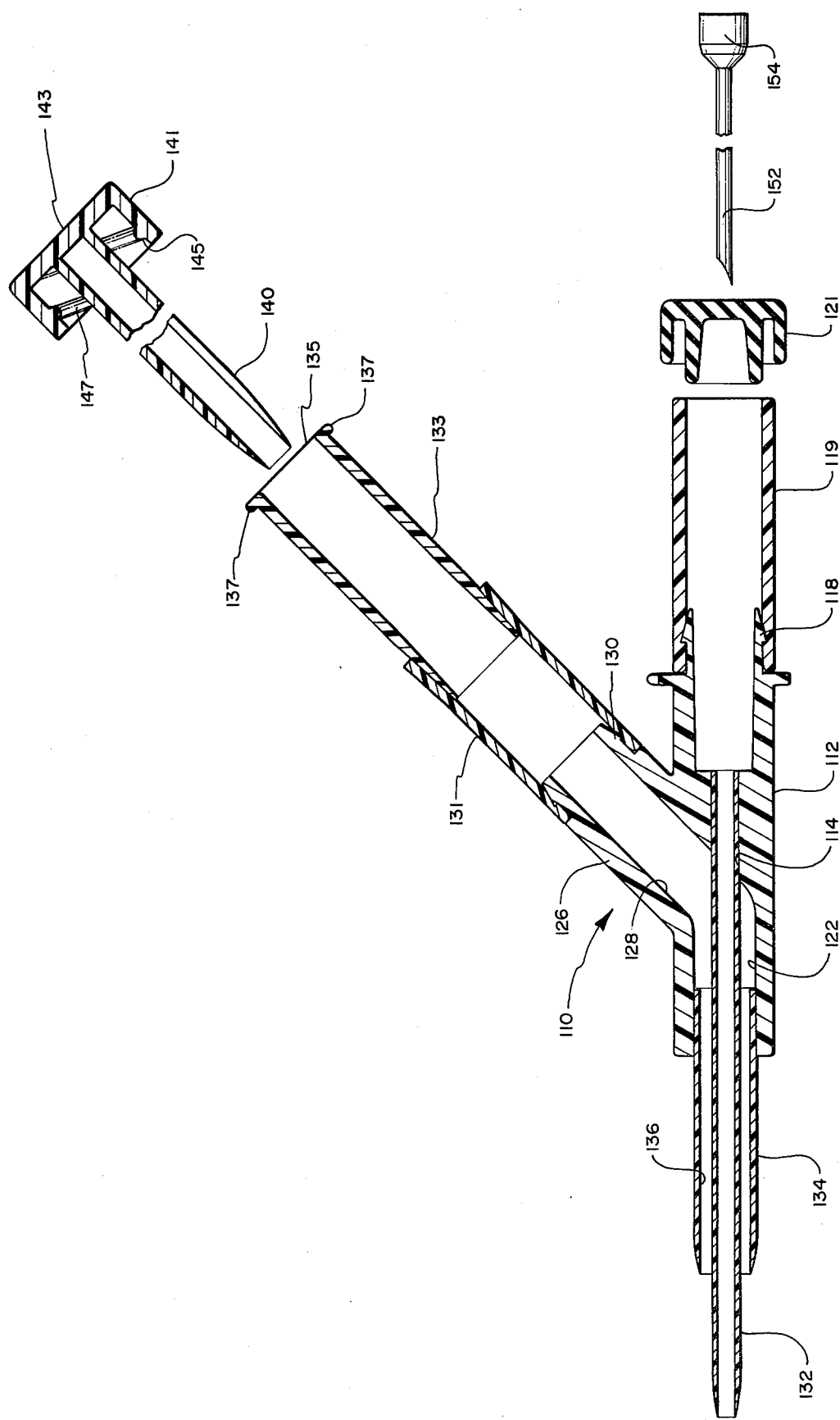
FIG. 4 is an exploded cross-sectional view of another presently preferred double lumen cannulae embodiment fragmentarily illustrating the stylet needle and bushing in the completely removed configuration.

Reference is now made to the embodiment of FIG. 4 which in many respects is similar to the embodiment of FIGS. 1–3. With continued reference to FIG. 4, the cannula assembly generally designated 110 comprises a hub 112 and a branch 126. The hub 112 has an axial bore 114 in which the interior cannula 132 is mounted in substantially the same manner as that described in connection with FIGS. 1–3 above. The branch 126 has a hollow 128 which is continuous with a diametrally enlarged bore 122 in the hub 112. The exterior cannula 134 is mounted within the bore 122 in the same manner as described in connection with FIGS. 1–3 above.

The embodiment of FIG. 4 differs in two principal respects. First, the trailing end 118 of the hub 112 is mounted to a flexible plastic sleeve 119 in fluid tight relation. The sleeve 119 has a penetrable self-sealing cap 121 which is removably secured to the trailing end of the sleeve 119 and through which the stylet needle 152 is initially penetrated.

The sleeve 119 advantageously accommodates the use of the cannula assembly 110 with a single needle dialysis system. For example, the stylet needle is used to introduce the assembly 110 into a patient's blood vessel. Thereafter, the stylet needle is axially withdrawn to the position illustrated in FIG. 4 out of the interior cannula 132. This permits blood to travel through the cannula 132 and into the sleeve 119. The self-sealing cap 121 prevents blood from spilling on the patient during the procedure. Thereafter, the flexible sleeve 119 can be suitably clamped while the cap 121 is removed preparatory to attachment of suitable blood flow lines to the sleeve 119. This procedure permits attachment of the assembly 110 to blood flow lines with minimum blood loss and inconvenience.

Similarly, the trailing end 130 of the branch 126 is mounted to a flexible sleeve 131. A rigid plastic adaptor is press-fit into the sleeve 131 and presents, at the trailing end 135 thereof, radially projecting Luer-lock dogs 137.

The flexible sleeve 131 provides essentially the same function as the flexible sleeve 119, i.e. the sleeve 131 may be finger-squeezed or clamped together to prevent outflow of blood through the passageway 136, hollow 128 and sleeve 131 during the period of time necessary to couple blood tubing the adaptor 133.

The adaptor 133 provides the second principal distinction between the embodiment of FIG. 4 and the embodiments of FIGS. 1–3. In this embodiment of FIG. 4, the bushing 140 is securely locked in place upon the adaptor 133 as will now be more fully described. When the bushing 140 is fully inserted into the passageway 136 so as to be superimposed upon the interior cannula 132 (see, for example, the position of bushing 40 in FIG. 1), cap 141 will be secured to the adaptor 133. The cap 141 is secured to the bushing 140 at 143 and has an interior hollow 145 which is slightly larger than the external diameter of the adaptor 133. Furthermore, the cap 141 has internal threads 147 which mate with the dogs 137 in a secure Luer-lock manner, as is conventional. Note that the rotation of the cap approximately one-quarter turn will free the cap 141 from the dogs 137 and permit withdrawal of the bushing 140 from the passageway 136. The bushing 140 is sufficiently flexible to permit rotation of the cap relative to the adaptor 133 the necessary amount to release the cap. Securement of the cap 141 to the adaptor 133 positively inhibits any rearward displacement of the bushing with respect to the cannulae 132 and 134 during venipuncture.

In the operation of the assembly 110, with the bushing 140 fully occupying the passageway 136 and with the stylet needle 152 in the fully inserted position (see, for example, corresponding structure in FIG. 1) the venipuncture is made. Note that the securement of the cap 141 with the adaptor 133 prevents the bushing 140 from being displaced rearwardly in the passageway 136 during venipuncture. After venipuncture, the bushing 140 is removed by rotating the cap 141 until the cap is disengaged from the Luer dogs 137. Preferably, the bushing 140 is removed from the passageway 136 before the needle 152 is extracted from the interior cannula 132. The reason for this preferred sequence is to utilize the stylet needle 152 to lend additional strength to the cannula 132 to counteract the resistance imposed as the bushing 140 is pulled around the cannula 132 during withdrawal. Thereafter, the stylet needle 152 is removed by axially displacing the needle through the cap 121.

Clearly, there is a closed and discrete flow channel formed by the interior cannula 132 and sleeve 119. There is a discrete and separate flow path created by the passageway 136, hollow 128 and sleeve 131.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A double lumen intravenous cannula assembly comprising in combination:
   an interior cannula;
   an exterior cannula surmounting the interior cannula and being spaced from at least a portion of the interior cannula to form a passageway therebetween;
   a hub mounted to said interior and exterior cannulae; and
   a removable sleeve-type bushing normally coaxially interposed in the passageway between the interior and exterior cannulae, said bushing extending through said hub and comprising an exteriorly accessible member displaceable to remove the bushing from the passageway.

2. A double lumen cannula assembly as defined in claim 1 comprising a hub having at least one branch, the interior cannula cooperating with the hub to form an axial passageway therethrough and the exterior cannula cooperating with the hub to form a passageway between the branch and the hollow of the exterior cannula.

3. A double lumen cannula assembly as defined in claim 2 wherein said bushing comprises an elongated flexible tube normally telescopically interposed between the interior and exterior cannulae and projecting through the branch of the hub, the bushing being removable from between the interior and exterior cannulae by withdrawing the bushing through the hub branch.

4. A double lumen cannula assembly as defined in claim 1 wherein said interior cannula projects forwardly beyond the leading end of the exterior cannula and wherein said bushing is tapered at its forward end to present an exterior cannula assembly contour which facilitates venipuncture.

5. A double lumen cannula assembly as defined in claim 1 further comprising an elongated needle telescopically interposed within the interior cannula projecting beyond the leading edge thereof to facilitate venipuncture, said needle having a diametral dimension which accommodates axial withdrawal of the needle from the double lumen cannula assembly after venipuncture.

6. A double lumen cannula assembly as defined in claim 2 wherein said hub and said branch both comprise coupling sites, the coupling site on said hub comprising exclusive fluid communication with the interior cannula and said coupling site on said branch providing exclusive fluid communication with the hollow of the exterior cannula.

7. A double lumen intravenous cannula assembly comprising in combination:
   a hub having an axial bore;
   an interior hollow cannula mounted upon the hub coaxially with the axial bore of the hub;
   an exterior hollow cannula mounted upon the hub coaxially with the axial bore of the hub, the exterior hollow cannula being diametrally enlarged and circumscribing at least a portion of the interior cannula and the interior cannula projecting beyond the leading end of the exterior cannula, the exterior and interior cannulae defining a space therebetween; and
   an elongated bushing extending through said hub and normally coaxially interposed in the space between the interior and exterior cannulae, said bushing comprising a finger-accessible member exterior of said hub and displaceable away from the hub so as to remove the bushing from the space between the interior and exterior cannulae even when the cannulae are both inserted into a blood vessel.

8. A double lumen cannula comprising in combination:
   a hub having a forward end and a trailing end and a bore axially disposed therethrough, said hub further comprising at least one angularly related branch, said branch also having a bore therethrough, the trailing end of the hub and the trailing end of the branch presented thereby both comprising coupling sites;
   an exterior cannula mounted upon the hub and communicating with the hollow of the branch;
   an interior cannula mounted upon the hub so as to be in axial alignment with the axial bore of the hub, said interior cannula being telescopically interposed within the exterior cannula and spaced therefrom so as to define a passageway between the interior and exterior cannulae, said interior cannula projecting beyond the leading end of the exterior cannula;
   an elongated flexible bushing removably interposed in the passageway between the interior and exterior cannula and extending somewhat beyond the leading end of the exterior cannula, the trailing end of the bushing traversing the hollow of the hub branch and comprising an exteriorly accessible member exposed outside of the hub branch and connected to the bushing, said bushing circumscribing a significant portion of the circumference of the interior cannula forward of the hub and a longitudinal slit formed in the bushing which longitudinal slit permits the bushing to be separated from the interior cannula when the bushing is withdrawn from the passageway between the interior and exterior cannulae through the hub branch;

a stylet needle normally telescopically interposed within the interior cannula so as to project slightly beyond the forward end thereof, the stylet needle being selectively removable from the interior cannula by axially displacing the stylet needle rearwardly away from the hub, the stylet needle, interior cannula, bushing and exterior cannula each cooperating to present a smooth surface for venipuncture and after venipuncture, the hub and cannulae permitting withdrawal of the stylet needle and withdrawal of the bushing so as to permit fluid flow through the interior cannula from the trailing end of the hub and also fluid flow through the exterior cannula through the branch of the hub.

* * * * *